US006350750B1

(12) United States Patent
Den Hartog et al.

(10) Patent No.: US 6,350,750 B1
(45) Date of Patent: Feb. 26, 2002

(54) QUINOLINE AND QUINAZOLINE DERIVATIVES HAVING CORTICOTROPIN RELEASING FACTOR (CRF) ANTAGONIST ACTIVITY

(75) Inventors: Jacobus A. J. Den Hartog; Gerben M. Visser; Johannes W. C. M. Jansen; Eric Ronken; Martinus T. M. Tulp; Jan H. Reinders, all of van Houtenlaan; Gerrit P. Toorop, deceased, late of van Houtenlaan, all of (NL), by Anna G. Toorop, heir

(73) Assignee: Duphar International Research B.V., Weesp (NL)

( * ) Notice: Subject to any disclaimer, the term of this patent is extended or adjusted under 35 U.S.C. 154(b) by 0 days.

(21) Appl. No.: 09/297,837

(22) PCT Filed: Sep. 7, 1998

(86) PCT No.: PCT/EP98/05726

§ 371 Date: Sep. 13, 1999

§ 102(e) Date: Sep. 13, 1999

(87) PCT Pub. No.: WO99/12908

PCT Pub. Date: Mar. 18, 1999

(30) Foreign Application Priority Data

Sep. 9, 1997 (EP) ............................................ 97202762

(51) Int. Cl.$^7$ .................... A61K 31/495; C07D 237/26; C07D 239/00; C07D 239/70; C07D 487/00
(52) U.S. Cl. .................. 514/252.03; 544/235; 544/253; 544/278
(58) Field of Search ..................... 514/252.03; 544/235, 544/253, 278; 546/1

(56) References Cited

FOREIGN PATENT DOCUMENTS

| WO | 9534563 | | 12/1995 |
| WO | 9729109 | | 8/1997 |
| WO | 9808846 | * | 3/1998 |
| WO | 9829397 | | 7/1998 |
| WO | 9835967 | | 8/1998 |
| WO | 9729109 | * | 10/1998 |
| WO | 9847874 | * | 10/1998 |

* cited by examiner

*Primary Examiner*—Richard L. Raymond
*Assistant Examiner*—Sudhaker B. Patel
(74) *Attorney, Agent, or Firm*—Stevens, Davis, Miller & Mosher, L.L.P.

(57) ABSTRACT

The present invention relates to novel compounds, to a method for the preparation of these novel compounds, to pharmaceutical compositions containing one or more of these compounds as an active component and to methods of using these in the treatment of stress-related disorders.

7 Claims, No Drawings

QUINOLINE AND QUINAZOLINE DERIVATIVES HAVING CORTICOTROPIN RELEASING FACTOR (CRF) ANTAGONIST ACTIVITY

The present invention relates to novel compounds, to a method for the preparation of these novel compounds, to pharmaceutical compositions containing one or more of these compounds as an active component and to methods of using these in the treatment of a wide range of stress-related disorders. The compounds have Corticotropin Releasing Factor (CRF) antagonist activity.

CRF, a 41 amino acid peptide, is the primary physiological regulator of proopiomelanocortin(POMC)-derived peptide secretion from the anterior pituitary gland (*Proc.Nat.Acad.Sci* (*USA*) 80:4851 (1983); *Science* 213:1394 (1981)). In addition to its endocrine role at the pituitary gland, immunohistochemical localization of CRF has demonstrated that the hormone has a broad extrahypothalamic distribution in the central nervous system. CRF is known to produce a wide spectrum of autonomic, electrophysiological and behavioural effects consistent with a neurotransmitter or neuromodulator role in brain. Both preclinical and clinical data (relating to CRF levels, effects of exogenously administered CRF and CRF receptor density) support the hypothesis that CRF has an important role in a wide range of stress-related disorders (see: *Exp. & Clin Endocrinology & Diabetes* 105(2):65 (1997); and *Proc.Soc.Exp.Biol.&Med* 215(1):1 (1997)).

There is evidence that CRF antagonist compounds and compositions, which can attenuate the physiological responses to stress-related phenomena, have potential therapeutic utility for the treatment of a wide range of stress-related disorders, such as depression, anxiety related diseases, post traumatic stress disorder, obsessive compulsive disorder, headache, eating and feeding disorders, anorexia nervosa, gastrointestinal diseases, irritable bowel syndrome, inflammatory diseases, immune suppression, HIV infections, Alzheimer's disease, hemorrhagic stress, drug and alcohol withdrawal symptoms, drug addiction and fertility problems.

It has now been found that the novel compounds having formula (I):

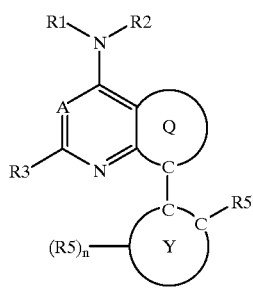

(I)

wherein

A is CH or N, ring Q is phenyl, pyridyl, pyrimidinyl or pyridazinyl, optionally substituted with one or two groups R4, ring Y is phenyl, pyridyl, pyrimidinyl, pyridazinyl or pyrazinyl, R1 and R2 are optionally branched $C_{1-6}$-alkyl, $C_{3-6}$-alkenyl, $C_{3-6}$-alkynyl, $C_{3-6}$-cycloalkyl-$C_{1-4}$-alkyl, phenyl-$C_{1-4}$-alkyl, 5- or 6-membered saturated or unsaturated heterocyclyl-$C_{1-4}$-alkyl, which groups R1 and R2 can be substituted with OH, $C_{1-3}$-alkoxy, $C_{1-3}$-alkoxycarbonyl, optionally mono- or di-($C_{1-3}$-alkyl) substituted amino, halogen or cyano, R3 is H, $C_{1-3}$-alkyl optionally substituted with one or more fluorine atoms; or R3 is halogen, methoxy or ethoxy, R4 is $C_{1-3}$-alkyl optionally substituted with one or more fluorine atoms, or R4 is halogen, methoxy, ethoxy, amino, mono- or di-substituted amino, or cyano, R5 is halogen, optionally branched $C_{1-6}$-alkyl, $C_{3-6}$-alkenyl, $C_{3-6}$-alkynyl, $C_{3-6}$-cycloalkyl -$C_{1-4}$-alkyl, O—($C_{1-6}$-alkyl), S—($C_{1-6}$-alkyl), $SO_2$—($C_{1-6}$-alkyl), hydroxy, cyano, nitro, trifluoromethyl, $SO_2NH_2$, $SO_2N$ (mono- or di-$C_{1-4}$-alkyl), formyl, CO—($C_{1-6}$-alkyl), COOH, COO—($C_{1-6}$-alkyl), CONH2, CON(mono- or di-$C_{1-4}$-alkyl), amino, N(mono or di-$C_{1-4}$-alkyl), NHCO($C_{1-6}$-alkyl), $NHSO_2$—($C_{1-6}$-alkyl), which groups R5 can be identical or different, and n has the value 0 to 4, with the proviso that the group $NR_1R_2$ is not diethylamino, ethyl,n-propylamino or ethyl,n-butylamino, if A is CH, Q is unsubstituted phenyl, $R_3$ is methyl, and substituent Y with the group(s) $R_5$ is 2,4,6-trimethylphenyl, and salts thereof have good CRF antagonist activity.

In vitro Receptor Binding Assay

The affinity of the compounds of the invention for the CRF receptor was determined by binding studies using membrane preparations of CC7-cells containing the human CRF receptor and [$^{125}$I]-ovine CRF as the ligand. Separation of bound and free ligand is performed by filtration over glassfiber-filters, essentially as described by H. Herdon et al, *Soc. Neurosci. Abstracts* 21(2),1349,1995.

Radioactivity on the filter is measured by liquid scintillation counting. Results are expressed as $IC_{50}$ values and transformed into inhibitory constants (Ki).

Assay for Functional CRF Antagonism

The antagonistic activity of the compounds of the invention was determined by functional studies using LVIP cells (*Mol. and Cell Neuroscience* 2:331, 1991). containing the rat CRF receptor. The origin of these cells is the mouse L-cell-line containing the cAMP responsive reporter gene construct coding for the enzyme β-galactosidase, which is subsequently transfected with the plasmid containing the genes coding for rat CRF.

Formation of cAMP is stimulated with rat CRF ($10^{-8}$M) for 3 hours. The increase of cAMP results in an increase in the production of β-galactosidase by stimulation of the reporter gene. The yellow product formed after administration of the substrate O-nitrophenyl-β-D-Galactopyranoside is measured spectrophotometrically (405 nm). Antagonistic activity can be obtained after a 30 minutes pre-incubation with putative antagonists and subsequent incubation with the (reference) antagonist CRF for 3 hours and is expressed as $pA_2$ values.

The novel quinoline and quinazoline derivatives of the present invention can be prepared by one of the general schemes outlined below (Scheme 1–2).

Key step in the construction of the desired 8-aryl substituted quin(az)oline derivatives is the Pd catalyzed Suzuki-Miyaura cross-coupling reaction (*Chem.Rev.* 95:2457, 1995). This Pd catalyzed C-C cross-coupling of relevant arylbromide precursors with aryl-boronic acid derivatives provides unique access to quin(az)oline derivatives with the substitution pattern required for CRF antagonistic activity.

Alternatively other cross-coupling methodology such as the Pd catalyzed Stille(Sn(alkyl)$_3$) reaction may also be applied (*Synthesis*, 803, 1992; *Advances in Metal-Organic Chemistry* 5:1, 1996)

Compounds of formula I wherein A is CH can be prepared as shown in Scheme 1.

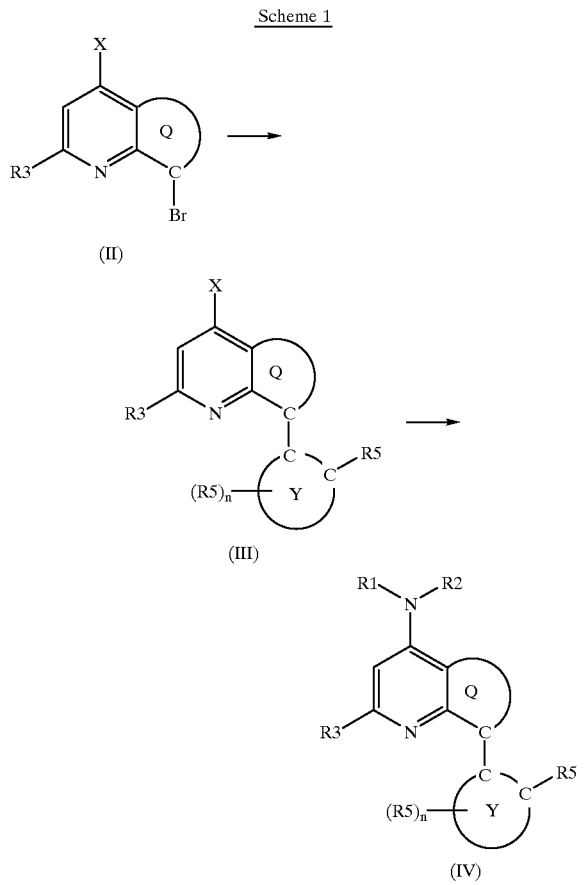

Starting from 4-hydroxy-8-bromo-quinoline derivatives (II), (X=OH) the 4-substituent can be converted into an appropriate leaving group such as X=Cl, OSO$_2$CH$_3$ or OSO$_2$C$_6$H$_4$—CH$_3$ by treatment with phosphorous oxychloride, methanesulfonylchloride or p-toluenesulfonylchloride. This intermediate may be further converted into an (optionally substituted) phenolate (X=OPhe) by treatment with (substituted) phenol. Compounds having formula (II) are known or can be prepared using known methods. In the next step an aryl-aryl coupling is performed between 8-bromo-quinoline derivatives (II) and the appropriate boronic acids Y'—B(OH)$_2$, wherein Y' has the same meaning as Y substituted with R5 and (R5)n. Depending on the meaning of group Q and/or Y, the Suzuki cross-coupling may also be carried out in reversed manner, i.e. using a quinoline boronic acid and the bromide Y'—Br. In still another way Stille (Sn(alkyl)$_3$) cross-coupling methodology may be applied to effect the desired C-C bond formation. In the final step the leaving group X is substituted with NR1R2 using the free amine NHR1R2 or the corresponding acetate as such, or using the same in a high boiling solvent, such as ethylene glycol, or in an aprotic solvent such as DMSO, THF, dioxane or DMF, facilitated by the optional use of a base such as K$_2$CO$_3$.

The final conversion of intermediates (III) wherein X is Cl may also be performed by application of a palladium catalyzed Buchwald-Hartwig reaction (*J.Am.Chem.Soc* 118, 1996, pg 7215, *J.Am.Chem.Soc.* 118,1996, pg 7217; *J.Am.Chem.Soc* 119, 1997, pg 8451) using the (secondary) amine NHR$_1$R$_2$ as the reagent in an aprotic solvent such as toluene, using a catalyst such as Pd$_2$(dibenzylideneacetone)$_3$, a base such as sodium tertiary butoxide and an additional ligand such as 2,2'-bis(diphenylphosphino)-1,1'-binaphtyl [BINAP]. Alternatively in the latter reaction the (primary) amine NH$_2$R$_1$ may be used, followed by an additional alkylation step with a halide R$_2$—Cl, R$_2$—Br or R$_2$—I to give compounds of formula IV.

Intermediates having formula III wherein R$_3$, Q, R$_5$, Y and n have the above meanings, and X is Cl or an optionally substituted phenoxy group are novel compounds suitable for the preparation of further interesting chemical compounds.

Compounds of formula I wherein A represents N can be prepared as shown in Scheme 2.

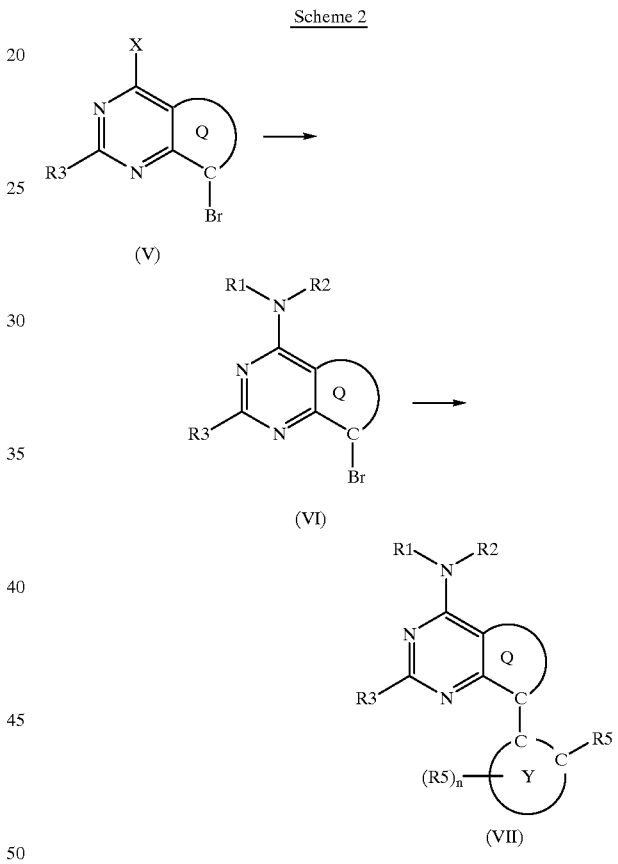

Starting from 4-hydroxy-8-bromo-quinazoline derivatives (V), (X=OH) the 4-substituent can be converted into an appropriate leaving group such as X=Cl, OSO$_2$CH$_3$ or OSO$_2$C$_6$H$_4$—CH$_3$ by treatment with phosphorous oxychloride, methanesulfonylchloride or p-toluenesulfonylchloride. Starting materials (X=OH) or intermediates (X=Cl) are known or can be prepared using known methods. In the next step the leaving group X is substituted with NR1R2 using the free amine NHR1R2 or the corresponding acetate as such, or using the same in a high boiling solvent, such as ethylene glycol, or in an aprotic solvent such as DMSO,THF, dioxane or DMF, facilitated by the optional use of a base such as K$_2$CO$_3$. In the final step aryl-aryl coupling is performed between 8-bromo-quinazoline derivatives (VI) and the appropriate boronic acids Y'—B(OH)$_2$, wherein Y' has the same meaning as Y substituted with R5 and (R5)n. Depending on the meaning of group Q and/or Y, the Suzuki cross-coupling may also be carried out in reversed fashion i.e. using a quinazoline boronic acid and the bromide Y'—Br. In still another way Stille (Sn(alkyl)$_3$) cross-coupling methodology may be applied to effect the desired C—C bond formation.

The invention is illustrated by means of the following examples.

EXAMPLE I

2-Methyl-4-(N-ethyl, N-n-butyl)amino-8-(2,4,6-tri-methylphenyl)-quinoline

Part A: To a quantity of 4.76 g (20 mmol) of 2-methyl-4-hydroxy-8-bromo-quinoline (*J.Org.Chem.* 1964, pg 3548) 15 ml of phosphorous oxychloride was added under ice-cooling. After heating to 100° C. for 30 minutes and subsequent cooling residual phosphorous oxychloride was removed by evaporation. After addition of ice water to the residue the mixture was neutralized with ammonia and extracted with $CH_2Cl_2$. The organic layer was dried over magnesium sulphate and concentrated in vacuo. The resulting product was purified on a silicagel column using ethylacetate as eluent. A total of 5.0 g of 2-methyl-4-chloro-8-bromo-quinoline was obtained (97% yield)

Part B: A mixture of 5.0 g (19.5 mmol) of 2-methyl-4-chloro-8-bromo-quinoline, 18.3 g (195 mmol) of phenol and 2.5 g (87%, 39 mmol) of KOH was heated at 120° C. under nitrogen for 30 min. After cooling 500 ml of $CH_2Cl_2$ was added and the mixture was extracted with 250 ml of 1N NaOH. After concentration of the organic layer in vacuo the residue was dissolved in ether and again extracted with 50 ml of 1N NaOH and 50 ml of brine. The organic layer was dried over magnesium sulphate and concentrated in vacuo. A total of 5.2 g of 2-methyl-4-phenoxy-8-bromo-quinoline was obtained as a white solid (85% yield).

Part C: To a solution of 5.2 g (16.5 mmol) of 2-methyl-4-phenoxy-8-bromo-quinoline in 175 ml DME-water (6:1), 3.3 g (20 mmol) of 2,4,6-tri-methyl-phenyl-boronic acid, 12.6 g (40 mmol) of $Ba(OH)_2.8H_2O$ and 0.46 g (0.4 mmol) of tetrakis(triphenylphosphine)palladium were added. After heating at 80° C. for 16 hours the mixture was cooled to room temperature, water was added and the mixture was extracted with $CH_2Cl_2$. The organic layer was dried over magnesium sulphate and concentrated in vacuo. The product was purified on a silicagel column using $CH_2Cl_2$ as the eluent. A total of 4.2 g of 2-methyl-4-phenoxy-8-(2,4,6-trimethylphenyl)-quinoline was obtained (73% yield)

Part D: A mixture of 4.2 g (12 mmol) of 2-methyl-4-phenoxy-8-(2,4,6-tri-methylphenyl)-quinoline and 29 g (180 mmol) of N-ethyl,N-n-butyl-ammonium acetate was heated at 160° C. under nitrogen while stirring for 6 hours. After cooling the mixture was dissolved in ether and extracted with 1N NaOH. The organic layer was dried over magnesium sulphate and concentrated in vacuo. The product was purified twice over silicagel using $CH_2Cl_2$/MeOH 95:5 and $CH_2Cl_2$/acetone 85:5, respectively, as the eluent. A total of 2.0 g of 2-methyl-4-(N-ethyl, N-n-butyl)amino-8-(2,4,6-trimethylphenyl)-quinoline was obtained (46% yield).

EXAMPLE II

2-Methyl-4-(N-2-morpholinoethyl,N-cyclopropylmethyl)amino-8-(2,4,6-tri-methylphenyl)-quinoline Part A: To a quantity of 4.76 g (20 mmol) of 2-methyl-4-hydroxy-8-bromo-quinoline (*J.Org.Chem.* 1964, pg 3548) 15 ml of phosphorous oxychloride was added under ice-cooling. After heating to 100° C. for 30 minutes and subsequent cooling residual phosphorous oxychloride was removed by evaporation. After addition of ice water to the residue the mixture was neutralized with ammonia and extracted with $CH_2Cl_2$. The organic layer was dried over magnesium sulphate and concentrated in vacuo. The resulting product was purified on a silicagel column using ethylacetate as eluent.

A total of 5.0 g of 2-methyl-4-chloro-8-bromo-quinoline was obtained (97% yield).

Part B: In a mixture of 270 ml dimethoxyethane and 45 ml water, after bubbling through nitrogen gas for 30 minutes, a quantity of 5.0 g ( 19.5 mmol) of 2-methyl-4-chloro-8-bromo-quinoline, 3.5 g (21 mmol) of 2,4,6-trimethyl phenylboronic acid, 13.2 g (42 mmol) $Ba(OH)_2.8H_2O$ and 0.69 g (0.6 mmol) tetrakis(triphenylphosphine)palladium were subsequently dissolved. After heating to 80° C. for 16 hours and subsequent cooling, 250 ml of water and 500 ml of $CH_2Cl_2$ were added. After separation the organic layer was dried over sodium sulphate and concentrated in vacuo. The product was purified on a silicagel column using dichloromethane as eluent. A total of 5.1 g of 2-methyl-4-chloro-8-(2,4,6-trimethylphenyl)-quinoline was obtained (88% yield).

Part C: To a solution of 5.1 g (17.1 mmol) of 2-methyl-4-chloro-8-(2,4,6-trimethylphenyl)-quinoline and 2.68 g (20.6 mmol) of 2-morpholinoethylamine in 150 ml of toluene, after bubbling through nitrogen gas for 30 minutes, a quantity of 2.29 g (23.9 mmol) sodium tertiary butoxide, 0.16 g (0.26 mmol) of 2,2'-bis(diphenylphosphino)-1,1'-binaphtyl (BINAP) and 0.082 g (0.09 mmol) $Pd_2$ (dibenzylideneacetone)$_3$ were subsequently added. After heating to 100° C. for 16 hours and subsequent cooling, the reaction mixture was filtered and concentrated in vacuo. The product was purified on a silicagel column using $CH_2Cl_2$/MeOH/NH$_4$OH 93:7:0.5 as the eluent. A total of 2.65 g of 2-methyl-4-(N-2-morpholinoethyl)amino-8-(2,4,6-tri-methylphenyl)-quinoline was obtained (40% yield).

Part D: To a solution of 2.65 g (6.8 mmol) 2-methyl-4-(N-2-morpholinoethyl)amino-8-(2,4,6-tri-methylphenyl)-quinoline in 60 ml dimethylformamide a quantity of 0.33 g (7.5 mmol; 55%) sodium hydride was added. After stirring for 30 minutes a quantity of 1.0 g (7.5 mmol) cyclopropylmethyl bromide was added and the reaction mixture was heated to 50° C. for 3 hours. After cooling to room temperature the mixture was poured in water and extracted with ethylacetate. The organic layer was extracted with brine, dried over magnesium sulphate and concentrated in vacuo.

The product was purified over silicagel using $CH_2Cl_2$/MeOH/NH$_4$OH 93:7:0.5 as the eluent. A total of 1.77 g of 2-methyl-4-(N-2-morpholinoethyl,N-cyclopropylmethyl)amino-8-(2,4,6-trimethylphenyl)-quinoline was obtained (60% yield).

In an analogous manner the compounds indicated in Table 1 are obtained. Formula (a) to (o) as used in Tables 1–3 for R6 have the following structure:

(a)
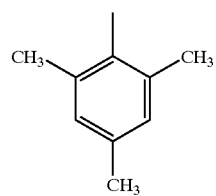
(b)
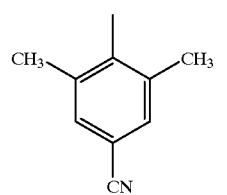
(c)
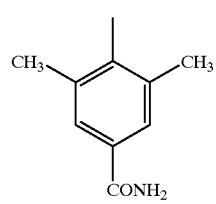
(d)
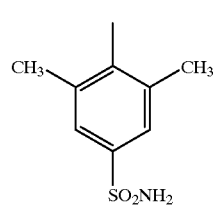
(e)
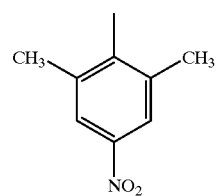
(f)
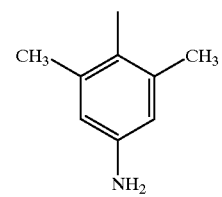
(g)
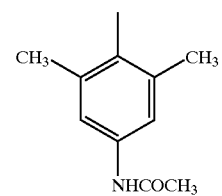
(h)
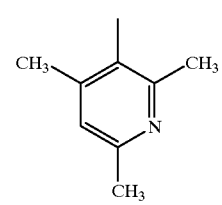
(i)
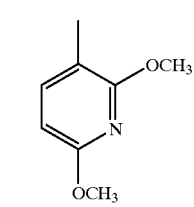
(j)
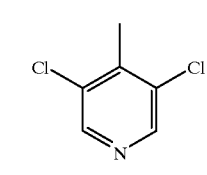
(k)
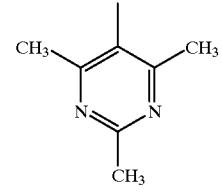
(l)
(m)
(n)

-continued

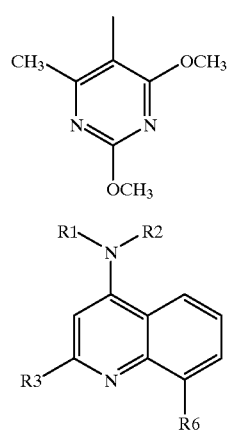

(o)

TABLE 1

| Comp. no. | R1 | R2 | R3 | R6 |
|---|---|---|---|---|
| 1 | n-propyl | cyclopropylmethyl | methyl | form. (a) |
| 2 | 2-CH₃O-ethyl | 2-CH₃O-ethyl | " | " |
| 3 | 2-N(CH₃)₂-ethyl | 2-N(CH₃)₂-ethyl | " | " |
| 4 | " | cyclopropylmethyl | " | " |
| 5 | " | ethyl | " | " |
| 6 | 2-piperidino-ethyl | cyclopropylmethyl | " | " |
| 7 | 4-pyridylmethyl | ethyl | " | " |
| 8 | n-butyl | ethyl | " | form. (b) |
| 9 | n-propyl | cyclopropylmethyl | " | " |
| 10 | 2-CH₃O-ethyl | 2-CH₃O-ethyl | " | " |
| 11 | 2-N(CH₃)₂-ethyl | 2-N(CH₃)₂-ethyl | " | " |
| 12 | " | cyclopropylmethyl | " | " |
| 13 | " | ethyl | " | " |
| 14 | 2-morpholinoethyl | cyclopropylmethyl | " | " |
| 15 | n-butyl | ethyl | H | form. (a) |
| 16 | " | " | H | form. (b) |
| 17 | n-propyl | cyclopropylmethyl | H | form. (a) |
| 18 | " | " | H | form. (b) |
| 19 | n-butyl | ethyl | CF₃ | form. (a) |
| 20 | " | " | " | form. (b) |
| 21 | n-propyl | cyclopropylmethyl | " | form. (a) |
| 22 | " | " | " | form. (b) |
| 23 | n-butyl | ethyl | CH₃ | form. (c) |
| 24 | n-propyl | cyclopropylmethyl | " | " |
| 25 | n-butyl | ethyl | " | form. (d) |
| 26 | n-propyl | cyclopropylmethyl | " | " |
| 27 | n-butyl | ethyl | " | form. (e) |
| 28 | n-propyl | cyclopropylmethyl | " | " |
| 29 | n-butyl | ethyl | " | form. (f) |
| 30 | n-propyl | cyclopropylmethyl | " | " |
| 31 | n-butyl | ethyl | " | form. (g) |
| 32 | n-propyl | cyclopropylmethyl | " | " |
| 33 | n-butyl | ethyl | " | form (h) |
| 34 | n-propyl | cyclopropylmethyl | " | " |
| 35 | n-butyl | ethyl | " | form (i) |
| 36 | n-propyl | cyclopropylmethyl | " | " |
| 37 | n-butyl | ethyl | " | form (j) |
| 38 | n-propyl | cyclopropylmethyl | " | " |
| 39 | n-butyl | ethyl | " | form (k) |
| 40 | n-propyl | cyclopropylmethyl | " | " |
| 41 | n-butyl | ethyl | " | form (l) |
| 42 | n-propyl | cyclopropylmethyl | " | " |
| 43 | n-butyl | ethyl | " | form (m) |
| 44 | n-propyl | cyclopropylmethyl | " | " |
| 45 | n-butyl | ethyl | " | form (n) |
| 46 | n-propyl | cyclopropylmethyl | " | " |
| 47 | n-butyl | ethyl | " | form (o) |
| 48 | n-propyl | cyclopropylmethyl | " | " |

EXAMPLE III

2-Methyl -4-(N-n-propyl,N-cyclopropylmethyl) amino-8-(2,4,6-trimethylphenyl)-8-(2,4,6-trimethylphenyl)-quinazoline Part A: A mixture of 19.2 g (89 mmol) of 2-amino-3-bromo benzoic acid (Beistein vol 14,369,vol IV,pg 1080) and 75 ml (0.79 mol) of acetic acid anhydride was heated to 110° C. under nitrogen with stirring for 3 hours. After cooling the mixture was concentrated in vacuo and co-evaporated twice with toluene. The product was purified over silicagel using CH₂Cl₂ as the eluent. A total of 17.0 g of 2-methyl-8-bromo-3,1-benzoxazin-4-one was obtained (80% yield).

Part B: A mixture of 17.0 g (71 mmol) of 2-methyl-8-bromo-3,1-benzoxazin4-one and 84.8 g (1.1 mol) of ammonium acetate was heated to 140° C. while stirring for 2 hours. After cooling to room temperature 250 ml of water was added under intensive stirring to the mixture. The resulting precipitate was collected by filtration and washed three times with 50 ml of water. The product was dried in vacuo, suspended in 150 ml of diisopropylether, stirred for 30 minutes and collected by filtration. The product was washed three times with diisopropylether and dried in vacuo resulting in a total of 14.2 g of 2-methyl-4-hydroxy-8-bromo-quinazoline (84% yield).

Part C: To a suspension of 14.2 g (59.5 mmol) of 2-methyl-4-hydroxy-8-bromo-quinazoline in 300 ml of benzene, 16 ml (120 mmol) of dimethylaniline and 6 ml (64 mmol) of phosphorus oxychloride were added under nitrogen. The light yellow solution resulting after heating to 80° C. while stirring was further heated at 80° C. for 3 hours. After cooling to room temperature 500 ml of benzene were added. The solution was extracted three times with 300 ml of 20% NaOH/water and 200 ml of water. The organic layer was dried over magnesium sulphate and concentrated in vacuo. The product was purified by column chromatography over silicagel using ether/petroleum-ether 1:9 as the eluent. A total of 12.3 g of 2-methyl-4-chloro-8-bromo-quinazoline was obtained as a white solid (80% yield).

Part D: A solution of 12.3 g (48 mmol) of 2-methyl-4-chloro-8-bromo-quinazoline, 8.0 ml (57 mmol) of N-n-propyl,N-cyclopropylmethyl-amine and 7.5 g (57 mmol) of K₂CO₃ in 100 ml of DMSO was stirred under nitrogen at room temperature for 16 hours. The mixture was poured into water and extracted three times with ether. After extraction with water the organic layer was dried over magnesium sulphate and concentrated in vacuo. The product was purified over silicagel using ether/petroleum ether 1:1 as the eluent. A total of 15.4 g of 2-methyl-4-(N-n-propyl,N-cyclopropylmethyl)amino-8-bromo-quinazoline was obtained as a colorless oil (95% yield).

Part E: To a solution of 15.4 g (46 mmol) of 2-methyl-4-(N-n-propyl,N-cyclopropylmethyl)amino-8-bromo-quinazoline in 400 ml of DME-water (7:1), 8.9 g (54 mmol) of 2,4,6-trimethyl-phenyl-boronic acid, 34.0 g (108 mmol) of Ba(OH)₂.8H₂O and 1.3 g (1.1 mmol) of tetrakis(triphenylphosphine)palladium were added. After heating at 85° C. for 21 hours the mixture was cooled to room temperature, water was added and the mixture was extracted three times with ethylacetate. The organic layer was extracted with brine, dried over magnesium sulphate and concentrated in vacuo. The product was purified over silicagel using CH₂Cl₂/MeOH 95:5 as the eluent. A total of 7.1 g of 2-methyl-4-(N-n-propyl,N-cyclopropylmethyl)amino-8-(2,4,6-trimethylphenyl)-quinazoline was obtained as a white solid (42% yield).

In an analogous manner the compounds indicated in Table 2 are obtained.

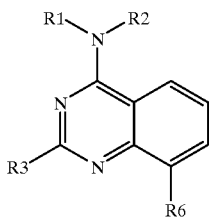

TABLE 2

| Comp. no. | R1 | R2 | R3 | R6 |
|---|---|---|---|---|
| 49 | n-butyl | ethyl | methyl | form. (a) |
| 50 | 2-CH$_3$O-ethyl | 2-CH$_3$O-ethyl | " | " |
| 51 | 2-N(CH$_3$)$_2$-ethyl | 2-N(CH$_3$)$_2$-ethyl | " | " |
| 52 | " | cyclopropylmethyl | " | " |
| 53 | " | ethyl | " | " |
| 54 | 2-mropholinoethyl | cyclopropylmethyl | " | " |
| 55 | n-propyl | 2-cyanoethyl | " | " |
| 56 | n-butyl | ethyl | " | form. (b) |
| 57 | n-propyl | cyclopropylmethyl | " | " |
| 58 | 2-CH$_3$O-ethyl | 2-CH$_3$O-ethyl | " | " |
| 59 | 2-N(CH$_3$)$_2$-ethyl | 2-N(CH$_3$)$_2$-ethyl | " | " |
| 60 | " | cyclopropylmethyl | " | " |
| 61 | " | ethyl | " | " |
| 62 | 2-morpholinoethyl | cyclopropylmethyl | " | " |
| 63 | n-butyl | ethyl | H | form. (a) |
| 64 | " | " | H | form. (b) |
| 65 | n-propyl | cyclopropylmethyl | H | form. (a) |
| 66 | " | " | H | form. (b) |
| 67 | n-butyl | ethyl | CF$_3$ | form. (a) |
| 68 | " | " | " | form. (b) |
| 69 | n-propyl | cyclopropylmethyl | " | form. (a) |
| 70 | " | " | " | form. (b) |
| 71 | n-butyl | ethyl | CH$_3$ | form. (c) |
| 72 | n-propyl | cyclopropylmethyl | " | " |
| 73 | n-butyl | ethyl | " | form. (d) |
| 74 | n-propyl | cyclopropylmethyl | " | " |
| 75 | n-butyl | ethy | " | form. (e) |
| 76 | n-propyl | cyclopropylmethyl | " | " |
| 77 | n-butyl | ethyl | " | form. (f) |
| 78 | n-propyl | cyclopropylmethyl | " | " |
| 79 | n-butyl | ethyl | " | form. (g) |
| 80 | n-propyl | cyclopropylmethyl | " | " |
| 81 | n-butyl | ethyl | " | form (h) |
| 82 | n-propyl | cyclopropylmethyl | " | " |
| 83 | n-butyl | ethyl | " | form (i) |
| 84 | n-propyl | cyclopropylmethyl | " | " |
| 85 | n-butyl | ethyl | " | form (j) |
| 86 | n-propyl | cyclopropylmethyl | " | " |
| 87 | n-butyl | ethyl | " | form (k) |
| 88 | n-propyl | cyclopropylmethyl | " | " |
| 89 | n-butyl | ethyl | " | form (l) |
| 90 | n-propyl | cyclopropylmethyl | " | " |
| 91 | n-butyl | ethyl | " | form (m) |
| 92 | n-propyl | cyclopropylmethyl | " | " |
| 93 | n-butyl | ethyl | " | form (n) |
| 94 | n-propyl | cyclopropylmethyl | " | " |
| 95 | n-butyl | ethyl | " | form (o) |
| 96 | n-propyl | cyclopropylmethyl | " | " |

Starting from similar compounds with analogous functionality as described above, the following compounds are synthesized:

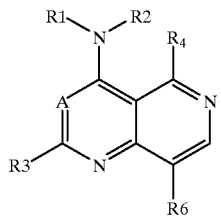

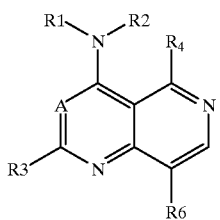

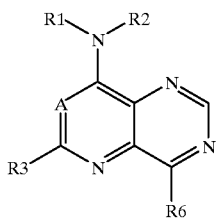

TABLE 3

| Comp. no. | formula | A | R1 | R2 | R4 | R6 |
|---|---|---|---|---|---|---|
| 97 | (p) | CH | ethyl | n-butyl | H | (a) |
| 98 | (p) | CH | n-propyl | cyclopropylmethyl | CH$_3$ | (a) |
| 99 | (p) | CH | ethyl | n-butyl | CH$_3$ | (b) |
| 100 | (p) | CH | n-propyl | cyclopropylmethyl | H | (b) |
| 101 | (p) | N | ethyl | n-butyl | CH$_3$ | (a) |
| 102 | (p) | N | n-propyl | cyclopropylmethyl | H | (a) |
| 103 | (p) | N | ethyl | n-butyl | H | (b) |
| 104 | (p) | N | n-propyl | cyclopropylmethyl | CH$_3$ | (b) |
| 105 | (q) | CH | ethyl | n-butyl | CH$_3$ | (a) |
| 106 | (q) | CH | n-propyl | cyclopropylmethyl | H | (a) |
| 107 | (q) | CH | ethyl | n-butyl | H | (b) |
| 108 | (q) | CH | n-propyl | cyclopropylmethyl | CH$_3$ | (b) |
| 109 | (q) | N | ethyl | n-butyl | H | (a) |
| 110 | (q) | N | n-propyl | cyclopropylmethyl | CH$_3$ | (a) |
| 111 | (q) | N | ethyl | n-butyl | CH$_3$ | (b) |
| 112 | (q) | N | n-propyl | cyclopropylmethyl | H | (b) |
| 113 | (r) | CH | ethyl | n-butyl | — | (a) |
| 114 | (r) | CH | n-propyl | cyclopropylmethyl | — | (a) |
| 115 | (r) | CH | ethyl | n-butyl | — | (b) |
| 116 | (r) | CH | n-propyl | cyclopropylmethyl | — | (b) |
| 117 | (r) | N | ethyl | n-butyl | — | (a) |
| 118 | (r) | N | n-propyl | cyclopropylmethyl | — | (a) |
| 119 | (r) | N | ethyl | n-butyl | — | (b) |
| 120 | (r) | N | n-propyl | cyclopropylmethyl | — | (b) |

What is claimed is:

1. Compound having formula I

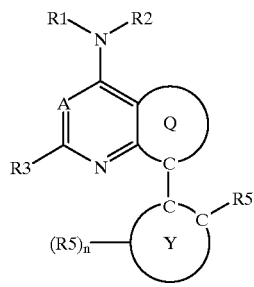

wherein:
A is CH,
ring Q is phenyl, pyridyl, pyrimidinyl or pyridazinyl, optionally substituted with one or two groups R4,
ring Y is phenyl, pyridyl, pyrimidinyl, pyridazinyl or pyrazinyl,
R1 and R2 are optionally branched $C_{1-6}$-alkyl, $C_{3-6}$-alkenyl, $C_{3-6}$-alkynyl, $C_{3-6}$-cycloalkyl-$C_{1-4}$-alkyl, phenyl-$C_{1-4}$-alkyl, 5- or 6-membered saturated or unsaturated heterocyclyl-$C_{1-4}$-alkyl, which groups R1 and R2 can be substituted with OH, $C_{1-3}$-alkoxy, $C_{1-3}$-alkoxycarbonyl, optionally mono- or di-($C_{1-3}$-alkyl) substituted amino, halogen or cyano,
R3 is H, $C_{1-3}$-alkyl optionally substituted with one or more fluorine atoms, or R3 is halogen, methoxy or ethoxy,
R4 is $C_{1-3}$-alkyl optionally substituted with one or more fluorine atoms, or R4 is halogen, methoxy, ethoxy, amino, mono- or di-substituted amino, or cyano,
R5 is halogen, optionally branched $C_{1-6}$-alkyl $C_{3-6}$-alkenyl, $C_{3-6}$-alkynyl, $C_{3-6}$-cycloalkyl-$C_{1-4}$-alkyl, O—($C_{1-6}$-alkyl), S—($C_{1-6}$-alkyl), $SO_2$—($C_{1-6}$-alkyl), hydroxy, cyano, nitro, trifluoromethyl, $SO_2NH_2$, $SO_2N$ (mono- or di-$C_{1-4}$-alkyl), formyl, CO—($C_{1-6}$-alkyl), COOH, COO ($C_{1-6}$-alkyl), $CONH_2$, CON(mono- or di-$C_{1-4}$-alkyl), amino, N(mono or di-$C_{1-4}$-alkyl), NHCO($C_{1-6}$-alkyl), $NHSO_2$—($C_{1-6}$-alkyl), which groups R5 can be identical or different, and
n has the value 0 to 4,
with the proviso that the group $NR_1R_2$ is not diethylamino, ethyl,n propylamino or ethyl,n-butylamino, if A is CH, Q is unsubstituted phenyl, R3 is methyl, and substituent Y with the group(s) R5 is 2,4,6-trimethylphenyl, and salts thereof.

2. Method for the preparation of compounds as claimed in claim 1, wherein A is CH characterized a) in that a compound having formula II

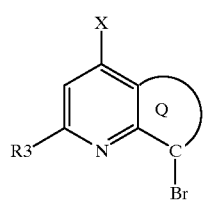

wherein R3 and Q have the meaning given in claim 1 and X is a so-called leaving group, is reacted with a boronic acid derivative of the formula Y'—$B(OH)_2$ wherein Y' has the same meaning as Y substituted with R5 and $(R5)_n$, and Y, R5 and n have the meaning given in claim 1, or b) in that in-stead of the bromine derivative (II) the corresponding boronic acid derivative is reacted with a compound of the formula Y'—Br, and converting the obtained compound (III)

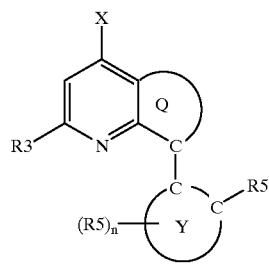

a) with an amine of the formula $HNR_1R_2$, or b) with an amine of the formula $R_1$—$NH_2$ followed by alkylation with a compound $R_2$—Cl, $R_2$—Br or $R_2$—I, into a compound having formula IV:

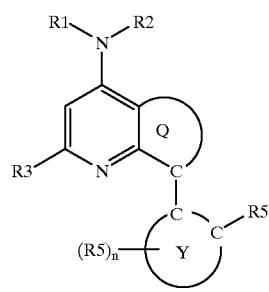

3. Compounds having formula III

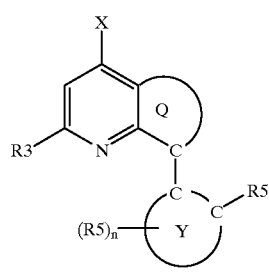

wherein $R_3$, Q, $R_5$, Y and n have the meanings given in claim 1, and X is Cl or an optionally substituted phenoxy group.

4. A method for the preparation of compounds as claimed in claim 1 wherein A is CH, and a) a compound having formula VI

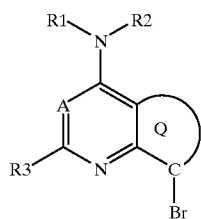

VI wherein R1–R3 and Q have the meaning given in claim 1, is reacted with a boronic acid derivative of the formula Y'—B(OH)$_2$, or b) instead of the bromine derivative (VI) the corresponding boronic acid derivative is reacted with a compound of the formula Y'—Br, in which formulae Y' is phenyl, pyridyl, pyrimidinyl, pyridazinyl or pyrazinyl; substituted with R5 wherein R5 has the meaning given in claim 1 to give a compound having formula VII:

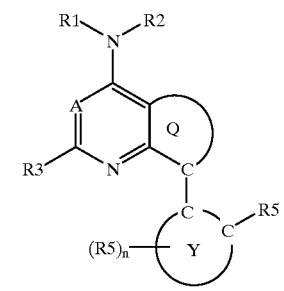

VII

5. A pharmaceutical composition comprising at least one compound according to claim 1 as active component.

6. A method of preparing a pharmaceutical composition comprising bringing an effective amount of at least one compound according to claim 1 in a form suitable for administration.

7. A method for attenuating the physiological responses to stress-related phenomena, comprising administering the composition of claim 5.

* * * * *